(12) United States Patent
Colvin, Sr. et al.

(10) Patent No.: US 9,901,497 B2
(45) Date of Patent: Feb. 27, 2018

(54) EMERGENCY LIGHTING AND FIRST AID STORAGE DEVICE

(71) Applicants: Walter Colvin, Sr., Holly Springs, NC (US); Cindy Colvin, Holly Springs, NC (US)

(72) Inventors: Walter Colvin, Sr., Holly Springs, NC (US); Cindy Colvin, Holly Springs, NC (US)

(*) Notice: Subject to any disclaimer, the term of this patent is extended or adjusted under 35 U.S.C. 154(b) by 174 days.

(21) Appl. No.: 14/959,188

(22) Filed: Dec. 4, 2015

(65) Prior Publication Data
US 2017/0156950 A1 Jun. 8, 2017

(51) Int. Cl.
*A61F 17/00* (2006.01)
*F21V 33/00* (2006.01)

(52) U.S. Cl.
CPC .......... *A61F 17/00* (2013.01); *F21V 33/0068* (2013.01)

(58) Field of Classification Search
CPC ........ A47B 96/16; A47B 43/003; A47G 1/16; A47G 1/1653; F16M 13/02; F16M 13/022; A61F 17/00; F21V 33/0068
USPC ......................................... 211/113
See application file for complete search history.

(56) References Cited

U.S. PATENT DOCUMENTS

| | | | |
|---|---|---|---|
| 577,204 A * | 2/1897 | Patten | A47B 61/00 211/88.01 |
| 2,119,700 A | 6/1938 | Burgess | |
| 2,307,992 A | 1/1943 | Calhoun | |
| 2,692,053 A | 10/1954 | Calhoun et al. | |
| 3,684,102 A | 8/1972 | Colter | |
| 3,713,614 A | 1/1973 | Taylor | |
| 4,109,980 A | 8/1978 | Brockman et al. | |
| 4,475,660 A * | 10/1984 | Cain | A47L 13/51 211/113 |
| 5,337,906 A * | 8/1994 | Digiulio | B43M 99/006 211/69.1 |
| 5,348,166 A * | 9/1994 | Lema | A47F 1/085 211/113 |
| 5,526,943 A * | 6/1996 | Thompson | A47B 81/00 211/119.004 |
| 5,755,338 A * | 5/1998 | vom Braucke | B43M 99/00 211/13.1 |
| 5,884,784 A * | 3/1999 | Betts, Sr. | B01L 9/00 206/278 |
| 6,464,086 B1 * | 10/2002 | Klein | A47B 96/16 211/35 |
| 6,874,624 B2 | 4/2005 | Redzisz | |
| 7,188,738 B2 * | 3/2007 | Stafford | G09F 7/08 211/10 |
| D550,493 S | 9/2007 | Coran | |
| D640,488 S | 6/2011 | Didehvar | |
| 8,267,252 B2 * | 9/2012 | Foreman | B65D 21/0204 206/462 |

(Continued)

*Primary Examiner* — Patrick D Hawn

(57) ABSTRACT

An emergency lighting and first aid storage device for storage of emergency lighting and first aid materials includes a panel that is rigid. A plurality of compartments is coupled to a front of the panel. Each compartment is differentially configured for storage of emergency lighting and first aid materials. A coupler is coupled to the panel. The coupler is configured to couple the panel to a vertical substrate. A plurality of hooks is coupled to the front proximate to a bottom of the panel. The hooks are configured for hanging of keys and key sets from the panel.

17 Claims, 5 Drawing Sheets

(56) References Cited

U.S. PATENT DOCUMENTS

| | | | | |
|---|---|---|---|---|
| 2003/0085246 A1* | 5/2003 | Reisman | ............... | B60R 7/043 |
| | | | | 224/275 |
| 2004/0140282 A1* | 7/2004 | Wang | ............... | A47F 7/146 |
| | | | | 211/113 |
| 2005/0230336 A1* | 10/2005 | Mundy | ............... | A47B 43/00 |
| | | | | 211/113 |

* cited by examiner

EMERGENCY LIGHTING AND FIRST AID STORAGE DEVICE

BACKGROUND OF THE DISCLOSURE

Field of the Disclosure

The disclosure relates to storage devices and more particularly pertains to a new storage device for storage of emergency lighting and first aid materials.

SUMMARY OF THE DISCLOSURE

An embodiment of the disclosure meets the needs presented above by generally comprising a panel that is rigid. A plurality of compartments is coupled to a front of the panel. Each compartment is differentially configured for storage of emergency lighting and first aid materials. A coupler is coupled to the panel. The coupler is configured to couple the panel to a vertical substrate. A plurality of hooks is coupled to the front proximate to a bottom of the panel. The hooks are configured for hanging of keys and key sets from the panel.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
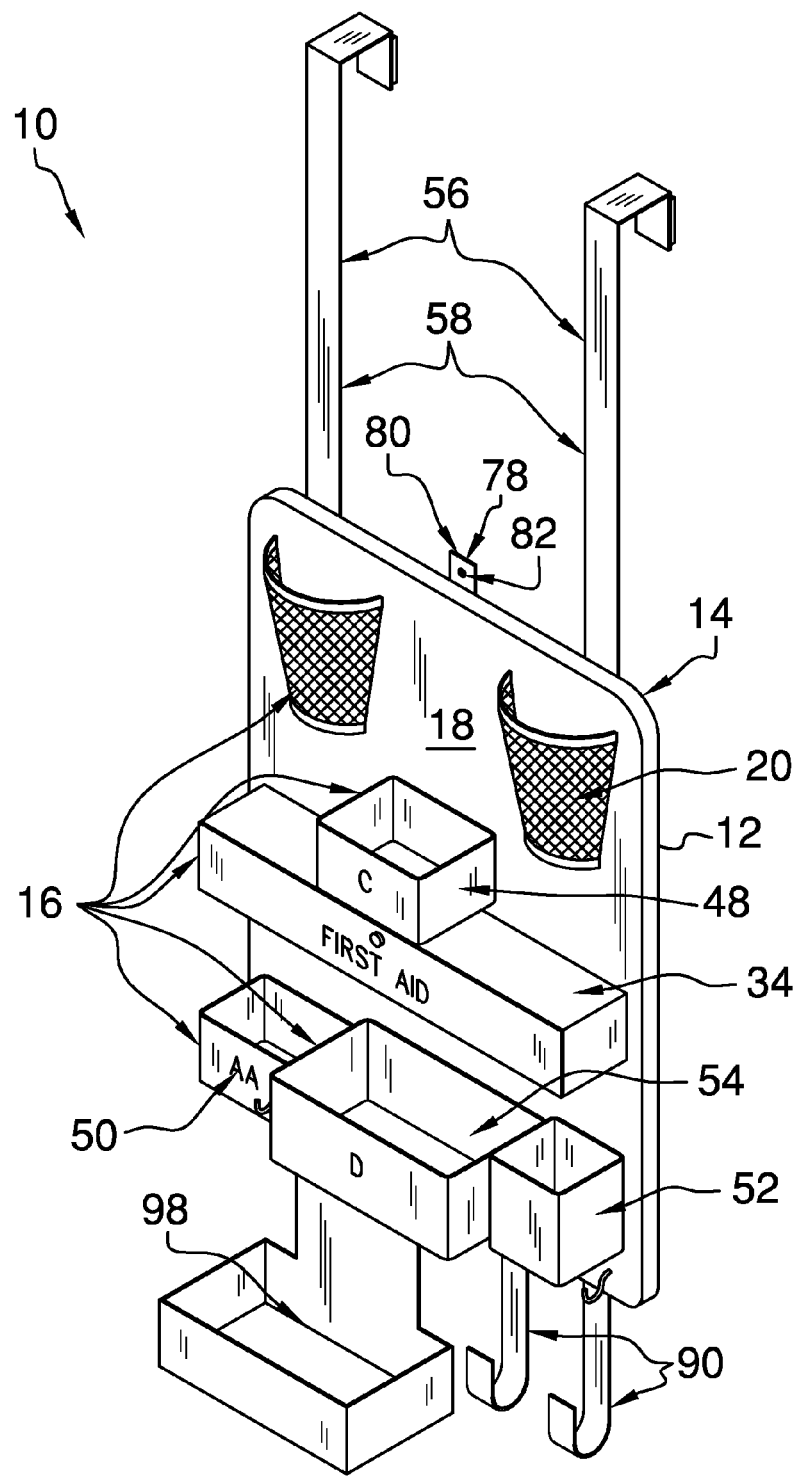
FIG. 1 is an isometric perspective view of an emergency lighting and first aid storage device according to an embodiment of the disclosure.
Figure 2:
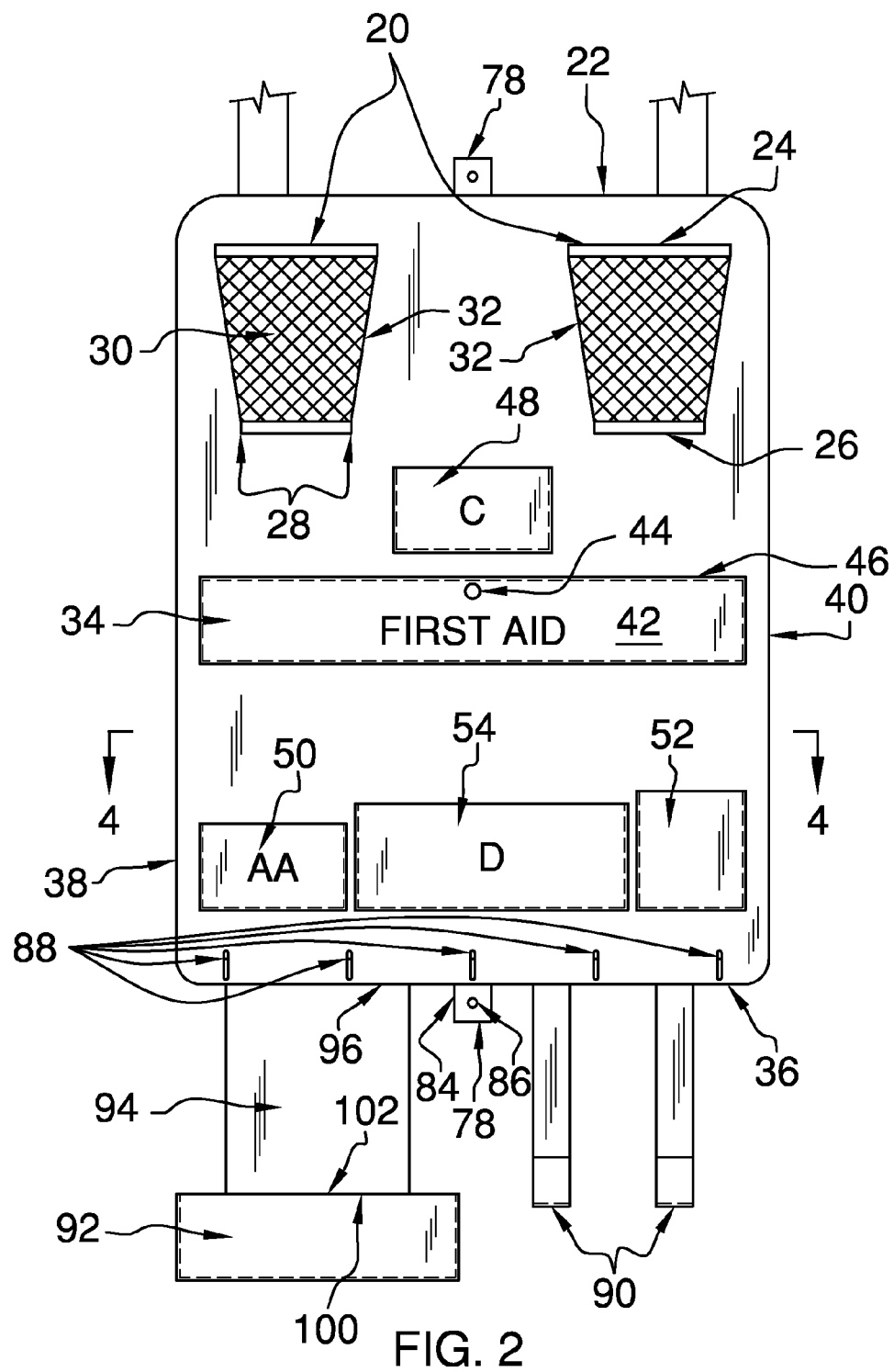
FIG. 2 is a front view of an embodiment of the disclosure.
Figure 3:
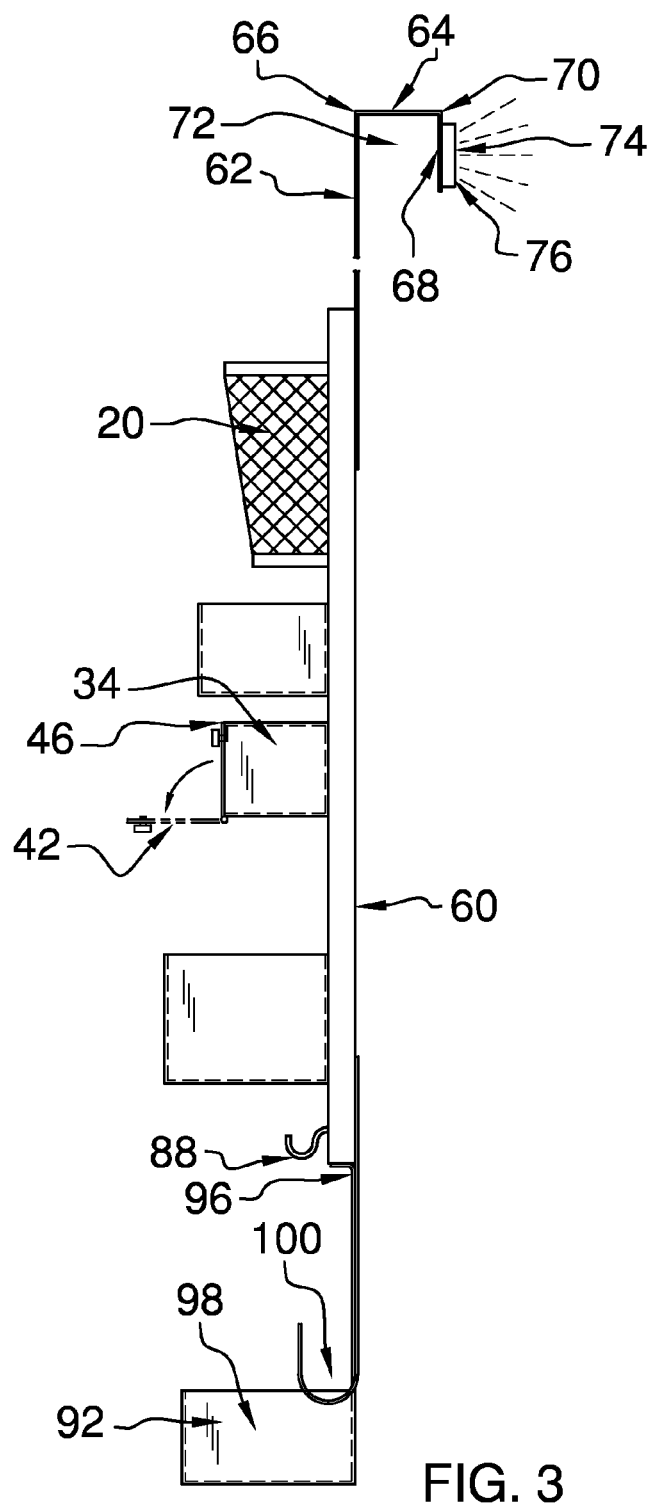
FIG. 3 is a right side view of an embodiment of the disclosure.
Figure 4:
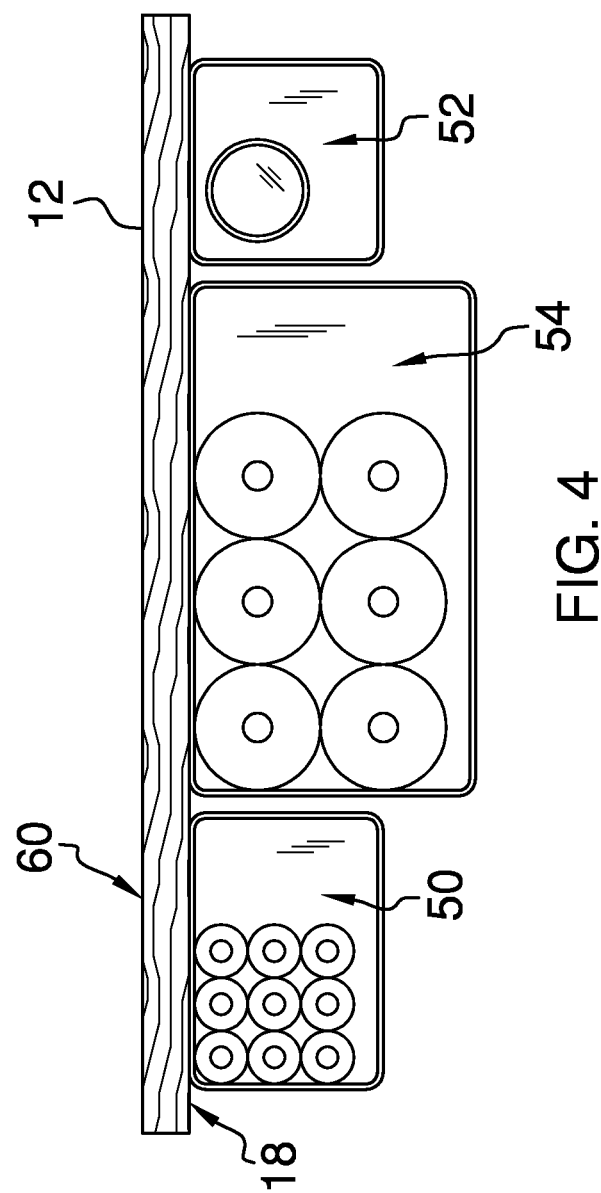
FIG. 4 is a detail view of an embodiment of the disclosure.
Figure 5:
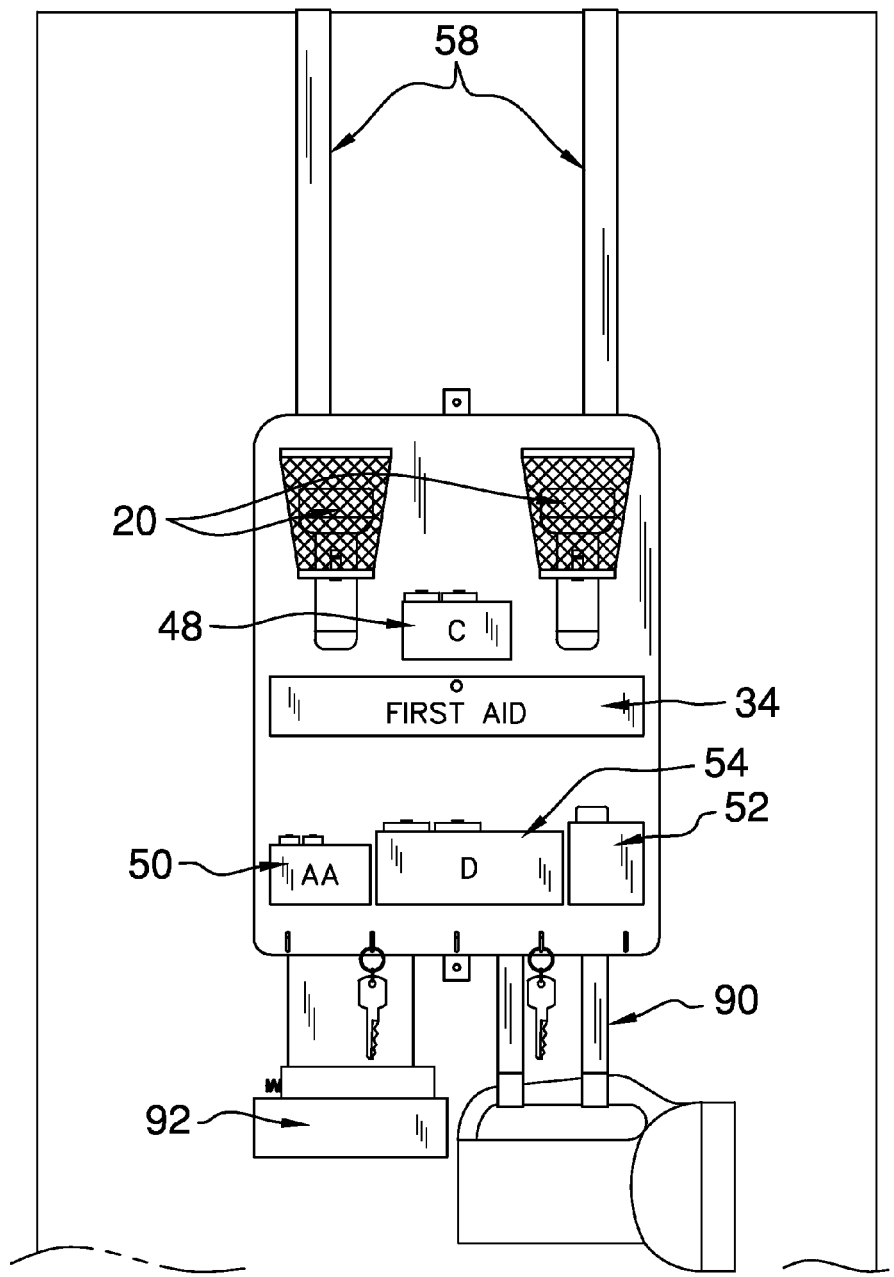
FIG. 5 is an in-use view of an embodiment of the disclosure.

With reference now to the drawings, and in particular to FIGS. 1 through 5 thereof, a new storage device embodying the principles and concepts of an embodiment of the disclosure and generally designated by the reference numeral 10 will be described.

As best illustrated in FIGS. 1 through 5, the emergency lighting and first aid storage device 10 generally comprises a panel 12 that is rigid. Preferably, the panel 12 is substantially rectangular and has rounded corners 14. A plurality of compartments 16 is coupled to a front 18 of the panel 12. Each compartment 16 is differentially configured for storage of emergency lighting and first aid materials.

More specifically, the plurality of compartments 16 comprises a pair of flashlight holders 20. The flashlight holders 20 are coupled to the front 18 proximate to a top 22. Each flashlight holder 20 comprises an upper rim 24 and a lower rim 26. The upper rim 24 and the lower rim 26 each have opposing ends 28 that are coupled to the front 18. The lower rim 26 is dimensionally smaller than the upper rim 24. Preferably, the upper rim 24 and the lower rim 26 are elastic. A mesh 30 extends between the lower rim 26 and the upper rim 24. The mesh 30 has edges 32 that are coupled to the front 18. The upper rim 24 and the lower rim 26 are arcuate, such that the flashlight holder 20 is half-cone shaped. The upper rim 24 is positioned for insertion of a flashlight. The flashlight engages the mesh 30, securing the flashlight in the flashlight holder 20.

A first aid storage unit 34 is coupled to the front 18 substantially equally distant from the top 22 and a bottom 36. The first aid storage unit 34 is elongated box shaped. The first aid storage unit 34 extends from proximate to a left side 38 to proximate to a right side 40 of the panel 12. The first aid storage unit 34 has a hinged front 42 that opens downwardly relative to the top 22. A knob 44 is positioned on the hinged front 42 proximate to an upper edge 46 of the first aid storage unit 34. The knob 44 is configured to be grasped by the user to open the hinged front 42 for access to the first aid storage unit 34.

A first battery storage unit 48 is coupled to the front 18 between the first aid storage unit 34 and the flashlight holders 20. The first battery storage unit 48 is configured for C-size battery storage. Preferably, the first battery storage unit 48 is sized to accommodate six C-sized batteries arranged two deep by three wide. A second battery storage unit 50 is coupled to the front 18 proximate to the left side 38 and between the first aid storage unit 34 and the bottom 36. The second battery storage unit 50 is configured for AA-size battery storage. Preferably, the second battery storage unit 50 is sized to accommodate fifteen AA-sized batteries arranged three deep by five wide. A mini-flashlight storage unit 52 is coupled to the front 18 proximate to the bottom 36 and the right side 40. The mini-flashlight storage unit 52 is configured for storage of small flashlights. A third battery storage unit 54 is coupled to the front 18 between the second battery storage unit 50 and the mini-flashlight storage unit 52. The third battery storage unit 54 is configured for D-size battery storage. Preferably, the third battery storage unit 54 is sized to accommodate eight D-sized batteries arranged two deep by four wide.

The first battery storage unit 48, the second battery storage unit 50, the third battery storage unit 54 and the mini-flashlight storage unit 52 each is open topped box shaped. The first battery storage unit 48, the second battery storage unit 50, the third battery storage unit 54, and the first aid storage unit 34 each is labeled, such that a user is noticed of the contents.

A coupler 56 is coupled to the panel 12. The coupler 56 is configured to couple the panel 12 to a vertical substrate. Preferably, the coupler 56 comprises a pair of brackets 58. The brackets 58 are coupled to the panel 12 and extend past the top 22 of the panel 12, such that the brackets 58 are configured to couple the panel 12 to a door. Preferably, the brackets 58 are coupled to a back 60 of the panel 12. One of the pair of brackets 58 is coupled proximate to the left side 38 of the panel 12 and the other of the pair of brackets 58 is coupled proximate to the right side 40 of the panel 12. Each bracket 58 comprises a vertical member 62 that is coupled to the back 60 of the panel 12 and extends past the top 22. The vertical member 62 is substantially coplanar with the panel 12. A horizontal member 64 is coupled to an end 66 of the vertical member 62 distal from the panel 12. The horizontal member 64 extends perpendicularly from the vertical member 62. A catch 68 is coupled to a terminus 70 of the horizontal member 64 distal from the vertical member 62. The catch 68 extends perpendicularly from the horizontal member 64. The vertical member 62, the horizontal member 64 and the catch 68 define an opening 72 that is complimentary to the profile of a door. The opening 72 is configured to be placed over the door to hang the panel 12.

A pair of lights 74 preferably comprises light emitting diodes 76. Each of the pair of lights 74 is coupled to a respective catch 68 of a respective bracket 58. When the panel 12 is configured on a door the lights 74 are visible on the opposing side of the door.

A pair of fasteners 78 is coupled to the panel 12. The fasteners 78 are configured to couple the panel 12 to a vertical substrate. The fasteners 78 comprises a first tab 80 that is coupled to the top 22 of the panel 12 equally distant from the left side 38 and the right side 40. A first hole 82 is centrally positioned in the first tab 80. A second tab 84 is coupled to the bottom 36 of the panel 12 equally distant from the left side 38 and the right side 40. A second hole 86 is centrally positioned in the second tab 84. The first hole 82 and the second hole 86 are configured to receive mounting hardware to secure the panel 12 to a vertical substrate.

A plurality of hooks 88 is coupled to the front 18 proximate to the bottom 36 of the panel 12. The hooks 88 are configured for hanging of keys or key sets from the panel 12. Preferably, the plurality of hooks 88 comprises five hooks. A pair of hangers 90 is coupled to the panel 12 and extends past the bottom 36 of the panel 12. The hangers 90 are configured for storage of a lantern type flashlight. The hangers 90 are positioned proximate to the right side 40 of the panel 12. The hangers 90 are U-shaped.

A fourth battery storage unit 92 is coupled to the bottom 36 proximate to the left side 38. The fourth battery storage unit 92 is configured for 6-volt battery storage. The fourth battery storage unit 92 comprises a plate 94 that has a top edge 96 coupled to the bottom 36 of the panel 12 proximate to the left side 38. An open box 98 that has an upper rim 100 is coupled to a bottom edge 102 of the plate 94.

In use, the pair of brackets 58 is positioned on the panel 12 such that the panel 12 can be hung from a door. Alternatively, the pair of fasteners 78 can be used to secure the panel 12 to a door or other vertical substrate. The plurality of compartments 16 are positioned on the front 18 of the panel 12 for storage of variously sized batteries and flashlights, as well as first aid materials. The pair of lights 74 is coupled to the catches 68 of the brackets 58, providing a guide to locate the device 10 during power outages.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. An emergency lighting and first aid storage device comprising:
    a panel, said panel being rigid;
    a plurality of compartments, said plurality of compartments being coupled to a front of said panel, each said compartment being differentially configured for storage of emergency lighting and first aid materials;
    a coupler, said coupler being coupled to said panel, wherein said coupler is configured to couple said panel to a vertical substrate, said coupler comprising a pair of brackets, said brackets being coupled to said panel and extending past a top of said panel, wherein said brackets are configured to couple said panel to a door, said brackets being coupled to a back of said panel, one of said pair of brackets being coupled proximate to a left side of said panel, the other of said pair of brackets being coupled proximate to a right side of said panel, each said bracket comprising
        a vertical member, each said vertical member being coupled to said back of said panel and extending past said top, said vertical member being substantially coplanar with said panel,
        a horizontal member, said horizontal member being coupled to an end of said vertical member distal from said panel, said horizontal member extending perpendicularly from said vertical member,
        a catch, said catch being coupled to a terminus of said horizontal member distal from said vertical member, said catch extending perpendicularly from said horizontal member, and
        wherein said vertical member, said horizontal member and said catch define an opening, said opening being complimentary to the profile of a door, such that said opening is configured to be placed over the door for hanging said panel;
    a pair of lights, each of said pair of lights being coupled to a respective catch of a respective said bracket, such that when said panel is configured on a door said lights are visible on the opposing side of the door; and
    a plurality of hooks, said hooks being coupled to said front proximate to a bottom of said panel, wherein said hooks are configured for hanging of keys and key sets from said panel.

2. The device of claim 1, further including said panel being substantially rectangular, said panel having rounded corners.

3. The device of claim 1, further including said plurality of compartments comprising:
    a pair of flashlight holders, said flashlight holders being coupled to said front proximate to a top of said panel;
    a first aid storage unit, said first aid storage unit being coupled to said front substantially equally distant from said top and said bottom, said first aid storage unit being elongated box shaped, said first aid storage unit extending from proximate to a left side to proximate to a right side of said panel, said first aid storage unit having a hinged front, said hinged front opening downwardly relative to said top;

a knob, said knob being positioned on said hinged front proximate to an upper edge of said first aid storage unit, such that said knob is configured for grasping to open said hinged front;

a first battery storage unit, said first battery storage unit being coupled to said front between said first aid storage unit and said flashlight holders, such that said first battery storage unit is configured for C-size battery storage;

a second battery storage unit, said second battery storage unit being coupled to said front proximate to said left side and between said first aid storage unit and said bottom, such that said second battery storage unit is configured for AA-size battery storage;

a mini-flashlight storage unit, said mini-flashlight storage unit being coupled to said front proximate to said bottom and said right side, said mini-flashlight storage unit being configured for storage of small flashlights;

a third battery storage unit, said third battery storage unit being coupled to said front between said second battery storage unit and said mini-flashlight storage unit, such that said third battery storage unit is configured for D-size battery storage.

4. The device of claim 3, further including each said flashlight holder comprising:

an upper rim and a lower rim, said upper rim and said lower rim each having opposing ends, said opposing ends being coupled to said front, said lower rim being dimensionally smaller than said upper rim, said upper rim and said lower rim being elastic;

a mesh, said mesh extending between said lower rim and said upper rim, said mesh having edges, said edges being coupled to said front;

said upper rim and said lower rim being arcuate, such that said flashlight holder is half-cone shaped; and wherein said upper rim is positioned for insertion of a flashlight with the flashlight engaging said mesh, such that the flashlight is secured in said flashlight holder.

5. The device of claim 3, further comprising:

said first battery storage unit being sized to accommodate six C-sized batteries arranged two deep by three wide;

said second battery storage unit being sized to accommodate fifteen AA-sized batteries arranged three deep by five wide; and said third battery storage unit being sized to accommodate eight D-sized batteries arranged two deep by four wide.

6. The device of claim 3, further including said first battery storage unit, said second battery storage unit, said third battery storage unit and said mini-flashlight storage unit each being open topped box shaped.

7. The device of claim 1, further including said first battery storage unit, said second battery storage unit, said third battery storage unit and said first aid storage unit each being labeled, such that a user is noticed of the contents.

8. The device of claim 1, further including said lights comprising light emitting diodes.

9. The device of claim 1, further including a pair of fasteners, said fasteners being coupled to said panel, said fasteners being configured to couple said panel to a vertical substrate.

10. The device of claim 9, further including said fasteners comprising:

a first tab, said first tab being coupled to a top of said panel equally distant from a left side and a right side of said panel;

a first hole, said first hole being centrally positioned in said first tab;

a second tab, said second tab being coupled to said bottom of said panel equally distant from said left side and said right side;

a second hole, said second hole being centrally positioned in said second tab; and wherein said first hole and said second hole are configured to receive mounting hardware to secure said panel to a vertical substrate.

11. The device of claim 1, further including said plurality of hooks comprising five hooks.

12. The device of claim 1, further including a pair of hangers, said hangers being coupled to said panel and extending past said bottom of said panel, wherein said hangers are configured for storage of a lantern type flashlight.

13. The device of claim 12, further including said hangers being positioned proximate to a right side of said panel.

14. The device of claim 12, further said hangers being U-shaped.

15. The device of claim 3, further including a fourth battery storage unit, said fourth battery storage unit being coupled to said bottom proximate to said left side, such that said fourth battery storage unit is configured for 6-volt battery storage.

16. The device of claim 15, further including said fourth battery storage unit comprising:

a plate, said plate having a top edge coupled to said bottom of said panel proximate to said left side; and an open box, said open box having an upper rim coupled to a bottom edge of said plate.

17. An emergency lighting and first aid storage device comprising:

a panel, said panel being rigid, said panel being substantially rectangular, said panel having rounded corners;

a plurality of compartments, said plurality of compartments being coupled to a front of said panel, each said compartment being differentially configured for storage of emergency lighting and first aid materials;

said plurality of compartments comprising:

a pair of flashlight holders, said flashlight holders being coupled to said front proximate to a top of said panel, each said flashlight holder comprising:

an upper rim and a lower rim, said upper rim and said lower rim each having opposing ends, said opposing ends being coupled to said front, said lower rim being dimensionally smaller than said upper rim, said upper rim and said lower rim being elastic, a mesh, said mesh extending between said lower rim and said upper rim, said mesh having edges, said edges being coupled to said front, said upper rim and said lower rim being arcuate, such that said flashlight holder is half-cone shaped, and wherein said upper rim is positioned for insertion of a flashlight with the flashlight engaging said mesh, such that the flashlight is secured in said flashlight holder;

a first aid storage unit, said first aid storage unit being coupled to said front substantially equally distant from said top and a bottom of said panel, said first aid storage unit being elongated box shaped, said first aid storage unit extending from proximate to a left side to proximate to a right side of said panel, said first aid storage unit having a hinged front, said hinged front opening downwardly relative to said top, a knob, said knob being positioned on said hinged front proximate to an upper edge of said first aid storage unit, such that said knob is configured for grasping to open said hinged front, a first battery storage unit, said first battery storage unit being coupled to said front between said first aid storage unit and said flashlight holders, such that said first battery storage unit is configured for C-size battery storage, said first battery storage unit being sized to accommodate six C-sized batteries arranged two deep by three wide, a second battery storage unit, said second battery storage unit being coupled to said front proximate to said left side and between said first aid storage unit and said bottom, such that said second battery storage unit is configured for AA-size battery storage, said second battery storage unit being sized to accommodate fifteen AA-sized batteries arranged three deep by five wide, a mini-flashlight storage unit, said mini-flashlight storage unit being coupled to said front proximate to said bottom and said right side, said mini-flashlight storage unit being configured for storage of small flashlights, and a third battery storage unit, said third battery storage unit being coupled to said front between said second battery storage unit and said mini-flashlight storage unit, such that said third battery storage unit is configured for D-size battery storage, said third battery storage unit being sized to accommodate eight D-sized batteries arranged two deep by four wide, said first battery storage unit, said second battery storage unit, said third battery storage unit and said mini-flashlight storage unit each being open topped box shaped;

said first battery storage unit, said second battery storage unit, said third battery storage unit and said first aid storage unit each being labeled, such that a user is noticed of the contents;

a coupler, said coupler being coupled to said panel, wherein said coupler is configured to couple said panel to a vertical substrate;

said coupler comprising a pair of brackets, said brackets being coupled to said panel and extending past a top of said panel, wherein said brackets are configured to couple said panel to a door, said brackets being coupled to a back of said panel;

one of said pair of brackets being coupled proximate to a left side of said panel, the other of said pair of brackets being coupled proximate to a right side of said panel;

each said bracket comprising:
  a vertical member, each said vertical member being coupled to said back of said panel and extending past said top, said vertical member being substantially coplanar with said panel,
  a horizontal member, said horizontal member being coupled to an end of said vertical member distal from said panel, said horizontal member extending perpendicularly from said vertical member,
  a catch, said catch being coupled to a terminus of said horizontal member distal from said vertical member, said catch extending perpendicularly from said horizontal member, and
  wherein said vertical member, said horizontal member and said catch define an opening, said opening being complimentary to the profile of a door, such that said opening is configured to be placed over the door for hanging said panel;

a pair of lights, said lights comprising light emitting diodes, each of said pair of lights being coupled to a respective catch of a respective said bracket, such that when said panel is configured on a door said lights are visible on the opposing side of the door;

a pair of fasteners, said fasteners being coupled to said panel, said fasteners being configured to couple said panel to a vertical substrate;

said fasteners comprising:
  a first tab, said first tab being coupled to said top of said panel equally distant from said left side and said right side,
  a first hole, said first hole being centrally positioned in said first tab,
  a second tab, said second tab being coupled to said bottom of said panel equally distant from said left side and said right side,
  a second hole, said second hole being centrally positioned in said second tab, and
  wherein said first hole and said second hole are configured to receive mounting hardware to secure said panel to a vertical substrate;

a plurality of hooks, said hooks being coupled to said front proximate to a bottom of said panel, wherein said hooks are configured for hanging of keys or key sets from said panel;

said plurality of hooks comprising five hooks;

a pair of hangers, said hangers being coupled to said panel and extending past said bottom of said panel, wherein said hangers are configured for storage of a lantern type flashlight;

said hangers being positioned proximate to a right side of said panel, said hangers being U-shaped;

a fourth battery storage unit, said fourth battery storage unit being coupled to said bottom proximate to said left side, such that said fourth battery storage unit is configured for 6-volt battery storage; and said fourth battery storage unit comprising:
  a plate, said plate having a top edge coupled to said bottom of said panel proximate to said left side, and
  an open box, said open box having an upper rim coupled to a bottom edge of said plate.

\* \* \* \* \*